United States Patent [19]
Yoshida et al.

[11] 3,988,213
[45] Oct. 26, 1976

[54] METHOD OF DISTILLING VINYL COMPOUNDS

[75] Inventors: Sadao Yoshida, Suita; Kunihiro Kubota, Takatsuki; Daizo Kobayashi, Osaka; Noboru Shimizu, Ibaraki; Takashi Ohara, Nishinomiya, all of Japan

[73] Assignee: Nippon Shokubai Kagaku Kogyo Co., Ltd., Osaka, Japan

[22] Filed: Oct. 1, 1974

[21] Appl. No.: 510,917

Related U.S. Application Data

[63] Continuation of Ser. No. 291,598, Sept. 25, 1972, abandoned.

[52] U.S. Cl. ............................. 203/9; 203/DIG. 21; 260/499; 260/990; 261/152
[51] Int. Cl.² ...................... B01D 3/34; C07C 7/18
[58] Field of Search ................. 261/152; 202/158; 203/8, 9, DIG. 10, DIG. 21; 260/499, 419, 990, 485 S, 525

[56] References Cited
UNITED STATES PATENTS 3,464,893   9/1969   Gorodetsky ...................... 202/158
3,717,553   2/1973   Otsuki et al. ...................... 202/158

*Primary Examiner*—Frank W. Lutter
*Assistant Examiner*—Frank Sever
*Attorney, Agent, or Firm*—Sherman & Shalloway

[57] ABSTRACT

A method of distilling a polymerizable vinyl compound selected from the group consisting of acrolein, methacrolein, acrylic acid, methacrylec acid, hydroxyethyl acrylate, hydroxyethyl methacrylate, hydroxypropyl acrylate, hydroxypropyl methacrylate, glycidyl acrylate and glycidyl methacrylate, the method comprising distilling the polymerizable vinyl compound in the presence of a polymerization inhibitor using a distillation tower having perforated trays without downcomers and wherein the temperature of the inner wall of the tower is maintained at a temperature sufficient to prevent the condensation of the vapor being distilled, whereby the polymerizable vinyl compound is distilled without the formation of polymer.

3 Claims, 2 Drawing Figures

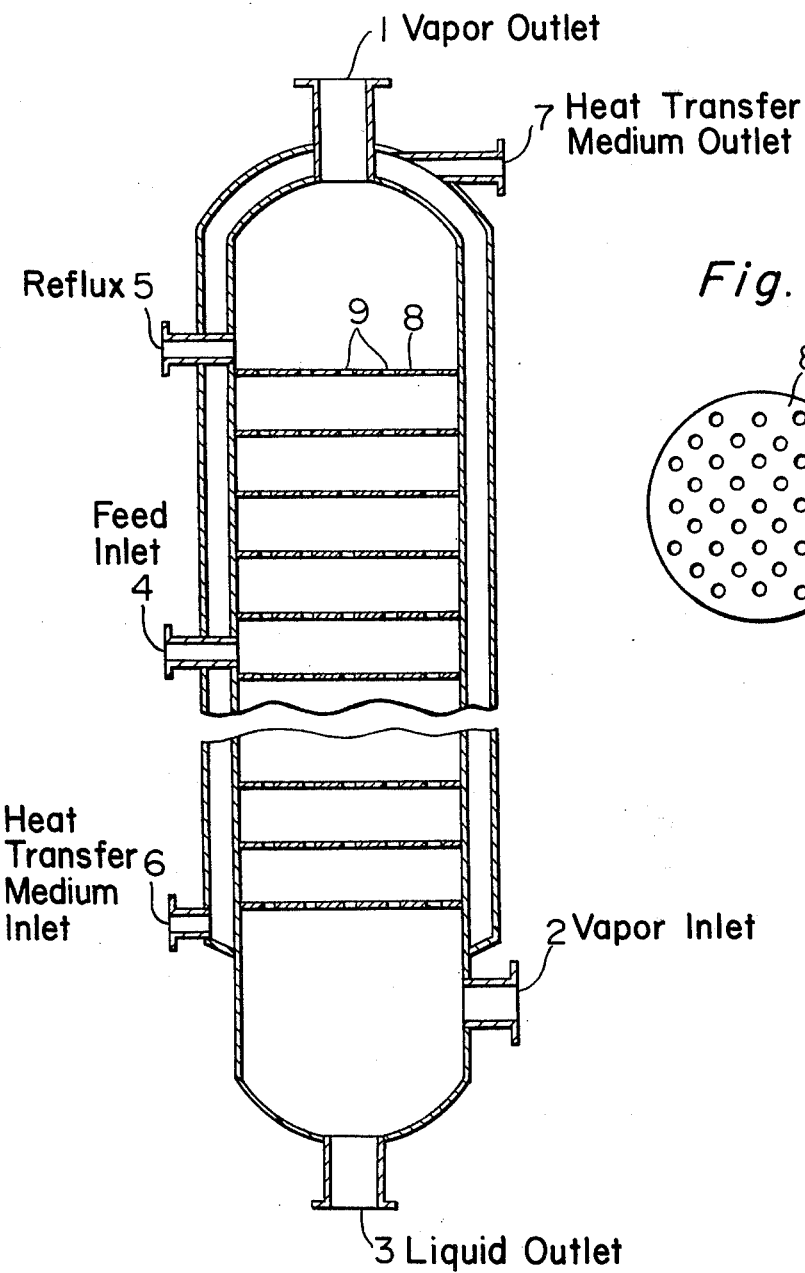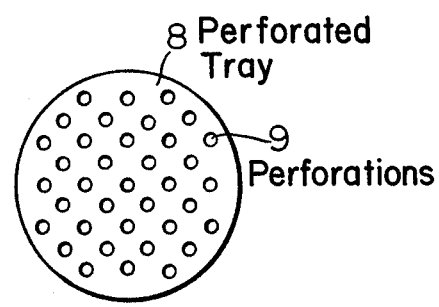

METHOD OF DISTILLING VINYL COMPOUNDS

This is a continuation of application Ser. No. 291,598, filed Sept. 25, 1972, now abandoned.

This invention relates to a method of distilling vinyl compounds. More specifically, the invention relates to a method of distilling a polymerizable vinyl compound selected from the group consisting of acrolein, mechacrolein, acrylic acid, methacrylic acid, hydroxyethyl acrylate, hydroxyethyl methacrylate, hydroxypropyl acrylate, hydroxypropyl methacrylate, glycidyl acrylate and glycidyl methacrylate, wherein the distillation of these compounds are carried out without the formation of the polymers of these compounds.

Of the known polymerizable vinyl compounds, the aromatic vinyl compounds such as styrene, the esters of unsaturated alcohols, such as vinyl acetate, the esters of unsaturated carboxylic acids, such as methyl acrylate and methyl methacrylate, and vinyl chloride are known as monomers having comparatively great stability, with the consequence that these monomers do not polymerize readily even though they are condensed from their vapor state. Hence, in the commercial production of these compounds, the distillation and purification operations can be carried out without taking into serious consideration such troubles as arise from the polymerization of these compounds.

On the other hand, of the polymerizable vinyl compounds, acrolein, methacrolein, acrylic acid, methacrylic acid, hydroxyethyl acrylate, hydroxyethyl methacrylate, hydroxypropyl acrylate, hydroxypropyl methacrylate, glycidyl acrylate and glycidyl methacrylate possess great polymerizability. Hence, in the purification of these compounds by distillation, polymerization takes place partially, and the distillation tower tends to become clogged by the polymer formed. Thus, it has been the practice in the past to carry out the distillation in the presence of a polymerization inhibitor such as hydroquinone or phenothiazine to prevent polymerization. However, these polymerization inhibitors, owing to their exceedingly low vapor pressure at the distillation temperature of the polymerizable vinyl compounds, give rise to such problems as described below.

That the vapor pressure of the polymerization inhibitor is exceedingly low at the distillation temperature of the polymerizable vinyl compounds means, in other words, that the liquid vinyl compounds condensed on the trays or packing of the distillation tower contain practically no polymerization inhibitor. The liquid vinyl compound in such a state is very instable. For instance, when the vinyl compound comes into contact with the rough surface inside the distillation tower or dwells in the tower for a prolonged period of time, it polymerizes partially. Once the polymerization is initiated in this manner it proceeds at an accelerated rate and results in the polymer formed clogging a part of the distillation tower formed. Hence, it frequently happens that the distillation operation must be stopped. This type of trouble can be reduced to a certain extent by the exercise of care in ensuring that the polymerization rate becomes slow by conducting the distillation operation at as low a distillation temperature as possible. However, as long as it is essentially impossible to avoid such a phenomenon to take place in various parts inside of the distillation tower, this kind of adjustment of the distillation operation does not provide a fundamental solution to the problem.

As a method of overcoming the shortcomings, such as noted above, that arise from the use of the usual polymerization inhibitors having a low vapor pressure, there is a proposal of conducting the distillation in the presence of a polymerization inhibitor having a high vapor pressure, as, for example, the organic nitroso compounds and hydrazine hydrate. However, while this type of polymerization inhibitor is effective in preventing the polymerization of the vinyl compounds during the distillation operation, there is the drawback that, as a natural outcome, they are inevitably contained in the distilled vinyl compounds as adulterants. Even though complicated operations are employed, considerable difficulty is experienced in eliminating these adulterant polymerization inhibitors from the vinyl compounds so adulterated. Further, even though it were possible to purify the vinyl compound to such an extent that only a trace of the polymerization inhibitor remains, this trace amount of polymerization inhibitor either becomes a hindrance in polymerizing the vinyl compound or becomes the cause of discoloration of the resulting polymer when the purified vinyl compound is used in preparing a polymer.

An object of the present invention is to provide a method which makes possible the distillation of the aforesaid specific vinyl compounds having great polymerizability, without experiencing the troubles such as hereinbefore described.

Other objects and advantages of the invention will become apparent from the following description.

The foregoing objects of the invention are achieved by carrying out the distillation of the aforesaid specific vinyl compounds in the presence of polymerization inhibitors in a distillation tower having perforated trays without downcomers, i.e., a multiplicity of trays having numerous perforations, which trays are disposed in spaced relationship and horizontally inside the tower, and by maintaining the temperature of the inner wall of the tower at a temperature sufficient to prevent the condensation of the vapor being distilled. The present invention was perfected on the basis of the presupposition that the aforesaid troubles that are encountered in the prior art can be completely eliminated even in those cases where the distillation is carried out using a polymerization inhibitor having a low vapor pressure, such as hydroquinone or phenothiazine, if the condensation liquid is made to contact the polymerization inhibitor-containing solution in the distillation tower at all times.

The packed tower, the bubble cap tray tower and the perforated tray tower are usually used as distillation towers in commercial plants. The following reasons for the use of a specific perforated tray tower according to the present invention, such as described above, will now be given.

In a packed tower it is impossible to effect a complete wetting of all parts of the packed layer, and there naturally are present parts which are not wetted by the polymerization inhibitor-containing solution. In consequence, the vinyl compound that has condensed at these parts starts to polymerize and, as a result, leads to clogging of the tower by means of the polymer formed. On the other hand, in the case of the bubble cap tray tower, the inner side of the cap, the bottom of the tray and the outer wall of the downcomer do not become wet, with a consequence that polymerization of the vinyl compound naturally takes place at these parts. Therefore, the use of either the packed tower or the bubble cap tray tower is not suitable for achieving the objects of the invention. In contradistinction, in the case of a tower having perforated trays without downcomer, i.e., a distillation tower made up of a multiplicity of trays having numerous perforations, which trays are disposed horizontally inside of the tower in spaced relationship, the top and bottom sides of the trays are always in a state of wetness by the solution and, since the condensation of the vapor takes place at the two sides of such trays, the possibility of polymerization taking place is very remote.

However, the objects of the present invention cannot be achieved by the use in customary manner of this distillation tower. The reason is that, as is well known, in the case of the distillation towers presently in actual use, regardless of their type, it is impossible to prevent completely the heat radiation from the inner side of the tower from the tower liquid by the mere insulation of the outer wall of the tower with lagging material, so long as the distillation is carried out at a temperature above room temperature. As a consequence, it is impossible to avoid the phenomenon of the condensation of the vapor at the inner wall of the tower during the distillation. However, it is vital to the achievement of the object of the invention that this phenomenon can be eliminated.

In the present invention, for eliminating this phenomenon, a means has been adopted of providing a heating apparatus at the outer wall of the tower thereby maintaining a temperature sufficient to prevent the condensation of the vapor that is being distilled.

The accompanying drawings illustrate one embodiment of a distillation tower for use in the process of the present invention, in which FIG. 1 is a longitudinal section of the distillation tower; and FIG. 2 is a plan view of the perforated tray without downcomer mounted within the distillation tower.

In the Figures, 1 represents a vapor outlet; 2, a vapor inlet (from reboiler); 3, a liquid outlet (to reboiler); 4, a sleeve for the delivery of feed; 5, a sleeve for reflux; 6, a heat transfer medium inlet; 7, a heat transfer medium outlet; 8, a perforated tray without downcomer; and 9, a perforation (hole) of the tray.

Generally, the temperatures at the various parts of the inside of the tower vary when carrying out the distillation of a material therein. Hence, it is almost impossible to achieve a state wherein the heat received and given off at the various parts of the inner wall of the tower are completely equalized. Thus, for maintaining the temperature of the inner wall in the present invention at the temperature sufficient to prevent the condensation of the vapor, it is necessary to heat the wall of the tower at a temperature somewhat higher than the temperature of the vapor being distilled in the tower. In this case, so long as the temperature of the inner wall of the tower is not made excessively higher than the temperature of the vapor inside the tower, there is practically no diminishment of the rectification effects. A difference in temperatures between the inner wall of the tower and the vapor inside the tower within 30° C is preferred.

As the source for heating the outer wall of the distillation tower, such known means as steam, electricity, hot air and hot water can be used. On the other hand, the method to be employed in heating the outer wall of the tower tray may be that in which the tower is divided into several sections and heated preferably by circulating the heating fluid through externally provided jackets or that in which the whole tower is heated in like manner.

The distillation is carried out at temperatures and pressures which are suited to the class of the polymerizable vinyl compound to be distilled. It may be carried out either batchwise or continuously.

The polymerizable vinyl compounds that can be applied in the invention method include acrolein, methacrolein, acrylic acid, methacrylic acid, hydroxyethyl acrylate, hydroxyethyl methacrylate, hydroxypropyl acrylate, hydroxypropyl methacrylate, glycidyl acrylate and glycidyl methacrylate.

The polymerization inhibitor that can be used in the invention method include those which are usually used, such as hydroquinone, phenothiazine, 4-tert.-butylcatechol, methylene blue, etc. These are either added to the crude vinyl compound to be distilled or into the distillation tower during distillation. Further, a trace amount of oxygen or air may also be introduced into the distillation tower from its bottom during distillation for promoting the effectiveness of these polymerization inhibitors.

Thus, it becomes possible in accordance with the present invention by operating in the manner described above on the basis of the principle hereinbefore described, to accomplish the distillation of the polymerizable vinyl compounds without the substantial formation of the polymers thereof. This will be specifically substantiated by the following (non-limiting) Examples.

EXAMPLE I

The distillation tower used was one provided with a jacket around its outer wall and having perforated trays without downcomer specified as follows; number of stages: 15, tray spacing: 250 mm, tray thickness: 2 mm, tray diameter: 150 mm, hole diameter: 10 mm. Acrylic acid was distilled by the total reflux method while adjusting the amount of reflux at 45 kilograms per hour at a tower top pressure of 40 mm Hg absolute. In the meanwhile hot water was introduced from the bottom of the jacket and discharged from the top to thus heat the tower wall. The temperature of the hot water was adjusted such that it was 80° C. at the bottom of the jacket and 70° C. at the top thereof.

On the other hand, fresh acrylic acid containing 2 % by weight of hydroquinone was added to the refluxing acrylic acid at rate of 500 grams per hour during the distillation operation, while withdrawing the old acrylic acid from the tower bottom at the rate of 500 grams per hour, thus maintaining the liquid level at the tower bottom constant. The temperatures of the bottom and top of the tower during the distillation operation were 78° and 66° C., respectively.

After having continued the total reflux distillation operation for 1200 hours in this manner, the tower was dismantled and examined. No polymer could be found in any part of the inside of the tower even after such a prolonged period of operation.

CONTROL I

When Example I was repeated except that hot water was not passed through the jacket, the temperature of the bottom of the tower, which was 78° C. at the start of the operation, rose to 90° C. after 150 hours. Further, on dismantling the tower, polymer was found to be adhering to the wall of the tower and the perforated trays, and considerable clogging of the perforations by the polymer was noted.

EXAMPLE II

A distillation tower of the same type as that used in Example I was used, and methacrylic acid was distilled by the total reflux method while adjusting the amount of reflux at 21.1 kilograms per hour at a tower top pressure of 10 mm Hg absolute. In the meanwhile the wall of the tower was heated by introducing hot water from the bottom of the jacket and discharging it from the top of the jacket. The temperature of the water at the bottom of the jacket was 83° and was 68° C. at the top thereof.

On the other hand, fresh methacrylic acid containing 1 % by weight of hydroquinone was added to the refluxing methacrylic acid at the rate of 500 grams per hour during the distillation operation, while withdrawing the old methacrylic acid from the tower bottom at the rate of 500 grams per hour. The temperatures of the bottom and top of the tower were respectively 80° and 60° C. during the distillation operation.

After 300 hours of continuous operation, the tower was dismantled. On examination of the inside of the tower, adhesion of polymer could not be noted anywhere therein.

EXAMPLE III

A distillation tower equipped with a jacket around its outer wall and having perforated trays without downcomer specified as follows; number of trays; 10, tray spacing: 250 mm, tray thickness: 2 mm, tray diameter: 80 mm, hole diameter: 5 mm, was used, and acrolein was distilled by the total reflux method while adjusting the amount of reflux at 45 kilograms per hour at normal atmospheric pressure. In the meanwhile hot water was introduced from the bottom of the jacket and discharged from the top thereof. The temperature of the hot water was 60° C. at the bottom of the jacket and 55° C. at the top thereof.

On the other hand, fresh acrolein containing 2 % by weight of hydroquinone was added at the rate of 500 grams per hour to the refluxing acrolein during the distillation operation, while from the bottom of the tower was withdrawn the old acrolein at the rate of 500 grams per hour. The temperatures of the bottom and top of the tower during the distillation operation were 53° and 52° C., respectively.

After having continued the total reflux distillation operation in this manner for 300 hours, the tower was dismantled and examined. No adhesion of polymer could be noted anywhere inside the tower.

EXAMPLE IV

A distillation tower of the same type as that used in Example III was used, and hydroxyethyl acrylate was distilled by the total reflux method while adjusting the amount of reflux at 5.5 kilograms per hour at a tower top pressure of 5 mm Hg absolute. In the meanwhile hot water was introduced from the bottom of the jacket and discharged from the top thereof. The temperature of the hot water was 100° C. at the bottom of the jacket and 85° C. at the top thereof.

On the other hand, fresh hydroxyethyl acrylate containing 1 % by weight of phenothiazine was added to the refluxing hydroxyethyl acrylate at the rate of 500 grams per hour during the distillation operation, while the old hydroxyethyl acrylate was withdrawn from the bottom of the tower at the rate of 500 grams per hour and air was introduced into the tower at the rate of 2 normal liter per hour from the tower bottom. The temperatures of the bottom and top of the tower during the distillation operation were 95° and 74° C., respectively.

After having continued the total reflux distillation operation in this manner for 100 hours, the tower was dismantled. On examination of the inside of the tower, no adhesion of polymer could be noted anywhere therein.

EXAMPLE V

A distillation tower of the same type as that used in Example III was used, and glycidyl methacrylate was distilled by the total reflux method while adjusting the amount of reflux at 6 kilograms per hour at a tower top pressure of 5 mm Hg absolute. In the meanwhile hot water was introduced from the bottom of the jacket and discharged from the top thereof. The temperature of the hot water was 85° C. at the bottom of the jacket and 73° C. at the top thereof.

On the other hand, fresh glycidyl methacrylate containing 1 % by weight of phenothiazine was added to the refluxing glycidyl methacrylate at the rate of 500 grams per hour during the distillation operation, while the old glycidyl methacrylate was withdrawn from the bottom of the tower at the rate of 500 grams per hour and air was introduced into the tower at the rate of 2 normal liter per hour from the bottom of the tower. The temperatures of the bottom and top of the tower during the distillation operation were 81° and 65° C., respectively.

After having continued the total reflux distillation operation in this manner for 100 hours, the tower was dismantled and examined. No adhesion of polymer could be noted anywhere inside of the tower.

What is claimed is:

1. In a method of distilling a polymerizable vinyl compound selected from the group consisting of acrolein, methacrolein, acrylic acid, methacrylic acid, hydroxyethyl acrylate, hydroxyethyl methacrylate, hydroxypropyl acrylate, hydroxypropyl methacrylate, glycidyl acrylate and glycidyl methacrylate, by distilling said polymerizable vinyl compound in contact with a polymerization inhibitor for said polymerizable vinyl compound in a distillation tower having perforated trays, the improvement comprising heating the tower to maintain the inner wall thereof at a temperature sufficiently high to prevent condensation of the vapor of the polymerizable vinyl compound being distilled but sufficiently low so as not to diminish the rectification effect of said tower, said temperature being within 30° C. higher than that of the vapor of said polymerizable vinyl compound being distilled, whereby formation of polymer of the polymerizable vinyl compound being distilled is prevented during distillation.

2. The method according to claim 1 wherein the temperature of the inner wall of the tower is maintained at a temperature within 11° C. of the temperature of the vapor of polymerizable vinyl compound being distilled by circulating a heated fluid through a jacket provided about the outer wall of said tower.

3. The method of claim 2 wherein the temperature of the inner wall of the tower is maintained at a temperature at least 2° C. higher than that of the temperature of the vapor of the polymerizable vinyl compound being distilled.

\* \* \* \* \*